US012121704B2

(12) United States Patent
Lesch et al.

(10) Patent No.: US 12,121,704 B2
(45) Date of Patent: *Oct. 22, 2024

(54) INJECTOR WITH ADJUSTABLE DOSING

(71) Applicant: Antares Pharma, Inc., Ewing, NJ (US)

(72) Inventors: Paul R. Lesch, Lino Lakes, MN (US); Matthew H. Rust, Hudson, WI (US); Thomas E. Kramer, Coon Rapids, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/930,950

(22) Filed: Sep. 9, 2022

(65) Prior Publication Data

US 2023/0001093 A1 Jan. 5, 2023

Related U.S. Application Data

(63) Continuation of application No. 16/713,837, filed on Dec. 13, 2019, now Pat. No. 11,471,600, which is a
(Continued)

(51) Int. Cl.
*A61M 5/20* (2006.01)
*A61M 5/30* (2006.01)
(Continued)

(52) U.S. Cl.
CPC ... *A61M 5/2033* (2013.01); *A61M 2005/2013* (2013.01); *A61M 2005/206* (2013.01);
(Continued)

(58) Field of Classification Search
CPC .. A61M 5/2033; A61M 5/30; A61M 5/31551; A61M 5/31563; A61M 2005/3125
(Continued)

(56) References Cited

U.S. PATENT DOCUMENTS

| 3,563,098 A | 2/1971 | Gley |
| 3,688,765 A | 9/1972 | Gasaway |

(Continued)

FOREIGN PATENT DOCUMENTS

| AR | 00081651 | 10/2012 |
| AR | 082053 | 11/2012 |

(Continued)

OTHER PUBLICATIONS

International Patent Application No. PCT/US14/23883, International Search Report, dated Jul. 10, 2014, 3 pages.
(Continued)

*Primary Examiner* — Michael J Tsai
*Assistant Examiner* — Nidah Hussain
(74) *Attorney, Agent, or Firm* — Morgan, Lewis & Bockius LLP (57) ABSTRACT

An injector for injecting a medicament in a patient. The injector includes a container comprising a fluid chamber containing a first volume of a medicament, and an injection conduit associated with the fluid chamber for defining a fluid pathway therefrom to inject the medicament from the fluid chamber through the injection conduit to an injection location. The injector also includes a firing mechanism associated with the fluid chamber for expelling the medicament from the fluid chamber through the injection conduit, arid a volume-control mechanism operable to control a fraction of the first volume of medicament that is injected when the firing mechanism is actuated to inject the medicament.

17 Claims, 3 Drawing Sheets

Related U.S. Application Data continuation of application No. 14/860,792, filed on Sep. 22, 2015, now Pat. No. 10,543,316, which is a continuation of application No. 12/299,288, filed as application No. PCT/US2007/068010 on May 2, 2007, now Pat. No. 9,144,648.

(60) Provisional application No. 60/796,942, filed on May 3, 2006.

(51) Int. Cl.
*A61M 5/31* (2006.01)
*A61M 5/315* (2006.01)
*A61M 5/32* (2006.01)
*A61M 5/42* (2006.01)

(52) U.S. Cl.
CPC ....... *A61M 5/30* (2013.01); *A61M 2005/3125* (2013.01); *A61M 5/31541* (2013.01); *A61M 5/31553* (2013.01); *A61M 5/31563* (2013.01); *A61M 5/3158* (2013.01); *A61M 5/31591* (2013.01); *A61M 5/3202* (2013.01); *A61M 5/326* (2013.01); *A61M 5/425* (2013.01)

(58) Field of Classification Search
USPC .......................................................... 604/68
See application file for complete search history.

(56) References Cited

U.S. PATENT DOCUMENTS

| | | |
|---|---|---|
| 3,712,301 A | 1/1973 | Sarnoff |
| 3,797,489 A | 3/1974 | Sarnoff |
| 3,882,863 A | 5/1975 | Sarnoff et al. |
| 4,484,910 A | 11/1984 | Sarnoff et al. |
| 4,558,690 A | 12/1985 | Joyce |
| 4,624,660 A | 11/1986 | Mijers et al. |
| 4,661,098 A | 4/1987 | Bekkering et al. |
| 4,664,653 A | 5/1987 | Sagstetter et al. |
| 4,678,461 A | 7/1987 | Mesa |
| 4,820,286 A | 4/1989 | van der Wal |
| 4,822,340 A | 4/1989 | Kamstra |
| 4,986,816 A | 1/1991 | Steiner et al. |
| 5,042,977 A | 8/1991 | Bechtold et al. |
| 5,062,830 A | 11/1991 | Dunlap |
| 5,078,680 A | 1/1992 | Sarnoff |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,393 A | 4/1992 | Sarnoff et al. |
| 5,114,406 A | 5/1992 | Gabriel et al. |
| 5,163,907 A | 11/1992 | Szuszkiewicz |
| 5,176,643 A | 1/1993 | Kramer et al. |
| 5,180,370 A | 1/1993 | Gillespie |
| 5,195,983 A | 3/1993 | Boese |
| 5,271,744 A | 12/1993 | Kramer et al. |
| 5,279,543 A | 1/1994 | Glikfeld et al. |
| 5,300,030 A | 4/1994 | Crossman et al. |
| 5,342,308 A | 8/1994 | Boschetti |
| 5,354,286 A | 10/1994 | Mesa et al. |
| 5,358,489 A | 10/1994 | Wyrick |
| 5,391,151 A | 2/1995 | Wilmot |
| 5,423,752 A * | 6/1995 | Haber ................... B01L 3/0234 604/82 |
| 5,425,715 A | 6/1995 | Dalling et al. |
| 5,478,316 A | 12/1995 | Bitdinger et al. |
| 5,514,097 A | 5/1996 | Knauer |
| 5,540,664 A | 7/1996 | Wyrick |
| 5,567,160 A | 10/1996 | Massino |
| 5,569,192 A | 10/1996 | van der Wal |
| 5,593,388 A | 1/1997 | Phillips |
| 5,599,302 A | 2/1997 | Lilley et al. |
| 5,658,259 A | 8/1997 | Pearson et al. |
| 5,665,071 A | 9/1997 | Wyrick |
| 5,695,472 A | 12/1997 | Wyrick |
| 5,820,602 A | 10/1998 | Kovelman et al. |
| 5,836,911 A | 11/1998 | Marzynski et al. |
| 5,843,036 A | 12/1998 | Olive et al. |
| 5,851,197 A | 12/1998 | Marano et al. |
| 5,891,085 A | 4/1999 | Lilley et al. |
| 5,891,086 A | 4/1999 | Weston |
| 5,919,159 A | 7/1999 | Lilley et al. |
| 5,935,949 A | 8/1999 | White |
| 6,045,534 A | 4/2000 | Jacobson et al. |
| 6,077,247 A | 6/2000 | Marshall et al. |
| 6,090,070 A | 7/2000 | Hager et al. |
| 6,099,504 A | 8/2000 | Gross et al. |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,241,709 B1 | 6/2001 | Bechtold et al. |
| 6,245,347 B1 | 6/2001 | Zhang et al. |
| 6,270,479 B1 | 8/2001 | Bergens et al. |
| 6,371,939 B2 | 4/2002 | Bergens et al. |
| 6,391,003 B1 | 5/2002 | Lesch, Jr. |
| 6,428,528 B2 | 8/2002 | Sadowski et al. |
| 6,517,517 B1 | 2/2003 | Farrugia et al. |
| 6,530,904 B1 | 3/2003 | Edwards et al. |
| 6,544,234 B1 | 4/2003 | Gabriel |
| 6,565,553 B2 | 5/2003 | Sadowski et al. |
| 6,569,123 B2 | 5/2003 | Alchas et al. |
| 6,569,143 B2 | 5/2003 | Alchas et al. |
| 6,607,508 B2 | 8/2003 | Knauer |
| 6,641,561 B1 | 11/2003 | Hill et al. |
| 6,656,150 B2 | 12/2003 | Hill et al. |
| 6,673,035 B1 | 1/2004 | Rice et al. |
| 6,682,504 B2 | 1/2004 | Nelson et al. |
| 6,746,429 B2 | 6/2004 | Sadowski et al. |
| 6,767,336 B1 | 7/2004 | Kaplan |
| 6,830,560 B1 | 12/2004 | Gross et al. |
| 6,912,417 B1 * | 6/2005 | Bernard ............... A61M 5/2033 604/20 |
| 6,932,793 B1 | 8/2005 | Marshall et al. |
| 6,932,794 B2 | 8/2005 | Giambattista et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,066,907 B2 | 6/2006 | Crossman et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,407,494 B2 | 8/2008 | Bostrom et al. |
| 7,416,540 B2 | 8/2008 | Edwards et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |

(56) References Cited

U.S. PATENT DOCUMENTS

| | | |
|---|---|---|
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,186 B2 | 7/2010 | Kohlbrenner et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 9,144,648 B2 | 9/2015 | Lesch, Jr. et al. |
| 11,471,600 B2 * | 10/2022 | Lesch .............. A61M 5/2033 |
| 2001/0039394 A1 | 11/2001 | Weston |
| 2002/0173752 A1 | 11/2002 | Polzin |
| 2003/0040697 A1 | 2/2003 | Pass et al. |
| 2003/0171717 A1 | 9/2003 | Farrugia et al. |
| 2004/0039337 A1 | 2/2004 | Letzing |
| 2004/0143213 A1 | 7/2004 | Hunter et al. |
| 2004/0220524 A1 | 11/2004 | Sadowski et al. |
| 2004/0267355 A1 | 12/2004 | Scott et al. |
| 2005/0027255 A1 | 2/2005 | Lavi et al. |
| 2005/0101919 A1 | 5/2005 | Brunnberg |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0100288 A1 | 5/2007 | Bozeman et al. |
| 2007/0123818 A1 | 5/2007 | Griffiths et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254035 A1 | 10/2009 | Kohlbrenner et al. |
| 2009/0292240 A1 * | 11/2009 | KraMer ............. A61M 5/3202 604/82 |
| 2009/0299278 A1 | 12/2009 | Lesch, Jr. et al. |
| 2009/0304812 A1 | 12/2009 | Stainforth et al. |
| 2009/0318361 A1 | 12/2009 | Noera et al. |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0204678 A1 | 8/2010 | Imran |
| 2010/0217105 A1 | 8/2010 | Yodfat et al. |
| 2010/0228193 A1 | 9/2010 | Wyrick |

(56) References Cited

U.S. PATENT DOCUMENTS

| | | |
|---|---|---|
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Charles |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |

(56) References Cited

U.S. PATENT DOCUMENTS

2013/0041347 A1  2/2013  Daniel
2013/0060231 A1  3/2013  Adlon et al.

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |

(56) References Cited

FOREIGN PATENT DOCUMENTS

| | | |
|---|---|---|
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 245895 | 11/1987 |
| EP | 255044 | 2/1988 |
| EP | 361668 | 4/1990 |
| EP | 525525 | 2/1993 |
| EP | 1067823 | 1/2001 |
| EP | 1307012 | 5/2003 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| GB | 2463034 | 3/2010 |
| IL | 171247 | 8/2012 |
| IL | 198750 | 10/2012 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |

(56) References Cited

FOREIGN PATENT DOCUMENTS

| | | |
|---|---|---|
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 94/11041 | 5/1994 |
| WO | WO 9831369 | 7/1998 |
| WO | WO 9832451 | 7/1998 |
| WO | WO 9922789 | 5/1999 |
| WO | WO 9962525 | 12/1999 |
| WO | WO 0006228 | 2/2000 |
| WO | WO 02/083216 | 10/2002 |
| WO | WO 02089805 | 11/2002 |
| WO | WO 03047663 | 6/2003 |
| WO | WO 3068290 | 8/2003 |
| WO | WO 03070296 | 8/2003 |
| WO | WO 03097133 | 11/2003 |
| WO | WO 2004/041331 | 5/2004 |
| WO | WO 2004/047892 | 6/2004 |
| WO | WO 2005/005929 | 1/2005 |
| WO | WO 2005/009515 | 2/2005 |
| WO | WO 2005/053778 | 6/2005 |
| WO | WO 2006/125328 | 11/2006 |
| WO | WO 2006/130098 | 12/2006 |
| WO | WO 2007/063342 | 6/2007 |
| WO | WO 2007/100899 | 9/2007 |
| WO | WO 2007/104636 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/100576 | 8/2008 |
| WO | WO 2008/107378 | 9/2008 |
| WO | WO 2009049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/042537 | 4/2011 |
| WO | WO 2011/042540 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/043714 | 8/2012 |
| WO | WO 2012/122643 | 9/2012 |
| WO | WO 2011/051366 | 5/2015 |

OTHER PUBLICATIONS

International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
International Patent Application No. PCT/US2007068010, International Search Report, dated Sep. 9, 2007, 3 pages.

* cited by examiner

INJECTOR WITH ADJUSTABLE DOSING

CROSS REFERENCE TO RELATED APPLICATIONS

This application is a continuation of U.S. patent application Ser. No. 16/713,837 filed Dec. 13, 2019, which is a continuation of U.S. patent application Ser. No. 14/860,792 filed Sep. 22, 2015, now U.S. Pat. No. 10,543,316, which is a continuation of U.S. Patent application Ser. No. 12/299,288 filed Jun. 3, 2009, now U.S. Pat. No. 9,144,648, which is a U.S. National Stage Entry of International Patent Application PCT/US2007/068010 filed May 2, 2007, which in turn claims the benefit of application of apriority from U.S. Provisional Patent Application No. 60/796,942 filed May 3, 2006, each of which is hereby incorporated by reference in its entirety.

FIELD OF THE INVENTION

The present invention relates to an injector, and more particularly to an injector with adjustable-dosing.

BACKGROUND OF THE PRESENT INVENTION

Injection devices for injection of medicaments into a patient are generally known. Such devices include, for example, traditional hypodermic needle syringes that contain a stock of medicament therein. Upon insertion of the needle under the patient's skin at an injection location, the medicament is forced out of the syringe and through the needle by depression of a plunger mechanism.

Injection devices also include needle-free injectors, some of which are described in U.S. Pat. Nos. 5,599,302 5,062,830; and 4,790,824; and needle-assisted. injectors, such as those described in U.S. Patent Publication No. 2005/0033234. These jet injectors administer medicaments as a fine, high velocity jet delivered under sufficient pressure to enable the jet to pass through the skin, or for improved dispersion of the injected medicament. Self-injectors car autoinjectors like the ones disclosed in U.S. Pat. Nos. 4,553,962 and 4,378,015, and PCT Publications WO 95/29720 and WO 97/14455 are constructed to inject medicament at a rate and in a manner similar to hand-operated hypodermic syringes.

These injectors often are made for a single use, or alternatively to be refilled after each injection. Some refillable injectors can be refilled with a desired dosage to be injected. Upon injection, the entire loaded dosage is injected.

An injector is needed that can deliver a medicament into a patient in an adjustable dose that is equal to or less than the full amount contained in the injector.

SUMMARY OF THE INVENTION

The invention is related to an injector. A preferred embodiment of the injector includes a container comprising a fluid chamber containing a first volume of a medicament, and an injection conduit associated with the fluid chamber for defining a fluid pathway therefrom to inject the medicament from the fluid chamber through the injection conduit to an injection location, The injector also includes a firing mechanism associated with the fluid chamber for expelling the medicament from the fluid chamber through the injection conduit, and a volume-control mechanism operable to control a fraction of the first volume of medicament that is injected when the firing mechanism is actuated to inject the medicament, Preferably, the volume-control mechanism is used to select a second volume, which is a portion or fraction of the first volume. The volume-control mechanism preferably includes a threaded ram that is biased by an energy source against a plunger and configured for rotating about a longitudinal axis of the injector. The volume-control mechanism also preferably includes a stopping member in threaded association with the ram and including at least one lateral member disposed within a track that extends longitudinally along a portion of the housing of the injector and is slidable therein. Preferably, the stopping member includes a pair of opposing lateral members, each disposed in separate opposing tracks, The lateral member prevents rotation of the stopping member about the longitudinal axis with the ram when the rani is rotated thereabout. The stopping member is configured for limiting movement of the ram along the longitudinal axis, the position of the stopping member being adjustable along the longitudinal axis with respect to the ram. The volume-control mechanism also includes a cap associated, and preferably removeably engageable, with the rain and configured for rotating the ram about the longitudinal axis to select an injection volume such that when the ram is rotated, the position of the stopping member is adjusted along the longitudinal axis with respect to the ram. Upon actuation of the energy source, which is preferably a spring, biasing of the ram against the plunger is preferably limited when the lateral member abuts the distal end of the track.

In one embodiment, the housing includes a transparent window adjacent the length of the track such that the longitudinal position of the stopping member within the injector is visible through the window. Preferably, the transparent window includes indicia corresponding to the position of the stopping member and the selected injection volume.

Preferably, the injector also includes a bearing member, such as an annular bushing or other bearing, disposed between the energy source and the ram, and configured for preventing or substantially reducing friction therebetween when the ram is rotated. The injector is preferably configured for single-use injection of medicament therefrom. Alternatively, the injector is configured for multiple injections of medicament therefrom.

In the preferred embodiment, the container is a prefilled syringe, and further includes an injection-assisting needle disposed in fluid communication with the fluid chamber, the needle having an injecting tip configured for piercing the patient's skin at the injection location. The housing houses the prefilled syringe and is configured for allowing insertion of the needle at the injection location to an insertion point that is at a penetration depth below the patient's skin. The injector preferably includes a syringe support supportively mounting the prefilled syringe to the housing. In other embodiments, the container is a needle-free cartridge, or a cartridge comprising an injection-assisting needle associated therewith.

In the preferred embodiment, the housing includes a retractable guard that is movable between a protecting position, in which the injection conduit is disposed within the guard, and an injecting position, in which the tip of the injection conduit is exposed for injection of the medicament at the injection location. A trigger mechanism is preferably operably associated with the energy source for actuation of the energy source to inject the medicament. Preferably, the trigger mechanism is configured for actuation of the energy source after the retractable guard is retracted from the protecting position. The retractable guard is preferably operably associated with the trigger mechanism to cause the trigger mechanism to activate the energy source when the guard is retracted to the injecting position.

The present invention thus provides an injector that enables a user to control or adjust the dose of medicament that is intended to be delivered to the patient.

DETAILED DESCRIPTION OF THE PREFERRED EMBODIMENTS

Figure 1:
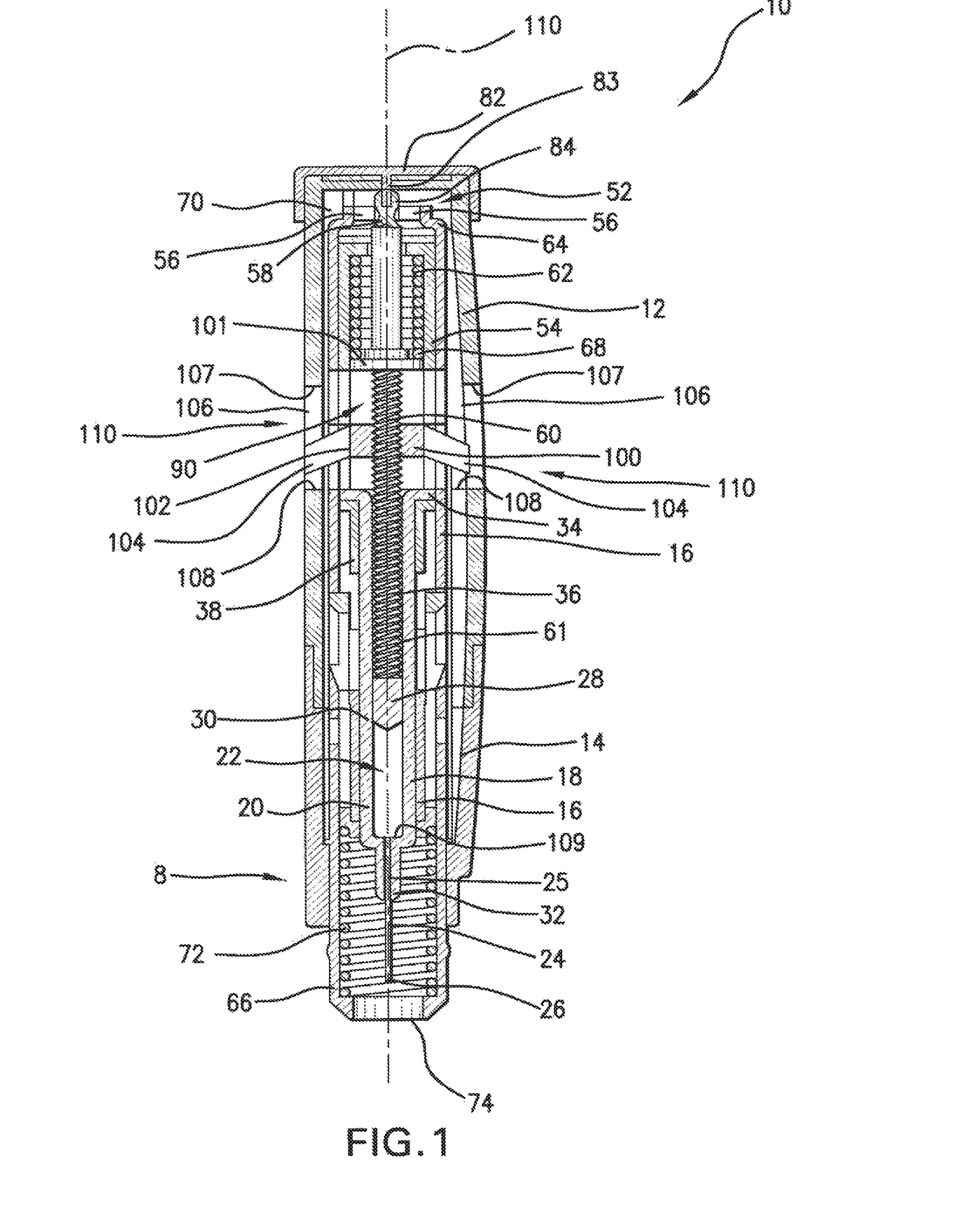
FIG. 1 is a cross-sectional view of a preferred embodiment of an injector constructed according to the present invention, showing the injector prior to injection.

Referring to FIG. 1, a preferred embodiment of an injector 10 has an outer housing 12 defined between a proximal end 6 and a distal end 8, and configured for allowing a user, typically the patient him or herself, to handle the injector 10 and position the injector near or adjacent an injection location. The outer housing 12 preferably houses most of the components of the injector 10. The injector 10 also includes a cover member 14 configured to associate with the outer housing 12 and cover the distal end of the injector 10 prior to use. A container support member 16 is housed within and mounted with the housing 12. The container support member 16 is configured to hold and position a container 18 within the injector 10. The container 18 can be, for example, a cartridge, syringe, or any other suitable container for holding medicament therein. In the preferred embodiment shown in FIG. 1, the container is a prefilled syringe 18. Alternatively, instead of a prefilled syringe attached to a needle, the syringe can have a separate needle that is associated and brought into fluid communication with the medicament container prior to or upon firing of the injector. In the preferred embodiment, the container support member 16 is substantially fixed to the outer housing 12, such as by snaps, an adhesive, a weld, or another known attachment. The container 18 has a container portion 20 that defines in its interior a fluid chamber 22, which is preferably prefilled with medicament to be injected. In another embodiment, however, this chamber can initially be provided empty.

At the distal end of the container 18 is an injection-assisting needle 24, which is in fluid communication with an injection port 25 of the fluid chamber 22. Needle 24 has an injecting tip 26 configured as known in the art to penetrate the tissue of a patient, preferably the skin, at the injection location. A needle bore extends through the needle 24, as known in the art. The bore is in fluid communication with the injection port 25 and the medicament in the fluid chamber 22, and is open at the needle tip 26 to inject the medicament.

In needle-free injector embodiments, the container does not include a needle and the injection port, of the fluid chamber preferably defines a fluid pathway in fluid communication with the fluid chamber for injecting medicament as a jet from the chamber through the port to the injection location. An example of a suitable needle-free jet nozzle arrangement is disclosed in U.S. Pat. No. 6,309,371.

At a proximal side of the fluid chamber 22, opposite from the needle 24, is a plunger 28 that preferably seals the medicament in the fluid chamber 22. A container wall 30 preferably comprises a tubular portion, preferably closed at a distal end and open at a proximal end, to define the fluid chamber 22. Plunger 28 is slideably received in the tubular portion. The container 18 is configured such that when the plunger 28 is displaced in a distal direction, the volume of the fluid chamber 22 is decreased, forcing the medicament out therefrom and through the injection port 25 and the bore of needle 24.

At the distal end of the fluid chamber 22 is a needle hub portion 32 to which the needle is mounted. A container flange 34 extends radially, preferably from the proximal end of the container wall 30.

In the preferred embodiment, the container 18 has a container body 36 that includes the flange 34, wall 30, and hub portion 32 of unitary construction. A preferred material for the container body 36 is glass, but other materials can be used in other embodiments, For example, a suitable prefilled syringe is the BD Hypak™, which is available in various sizes and volumes and is sold prefilled with medicament. The glass of the syringe body is adhered to the needle. Typical medicaments and medicament categories include epinephrine, atropine, sumatriptan, antibiotics, antidepressants, and anticoagulants.

In some embodiments, the injector includes a container cushion configured for providing additional support to the container within the housing, such as disclosed in International Application No. PCT/US2006/0002429, now WO 2006/079064, The container cushion 38 is preferably made of an elastomeric material or other resilient material. A flange of the container cushion 38 extends radially and is disposed and serves as an interface between the distal side of the container support member 16 and the container flange 34. Elevated portions, such as nubs, preferably extend proximately from the cushion flange and are configured and dimensioned to abut the container flange 34. A sleeve portion of the container cushion 38 extends axially around the interior of the container support 16. The container cushion 38 is preferably received in the interior of the container support 16 and receives the container body 36, preferably fitting snugly therein.

Figure 2:
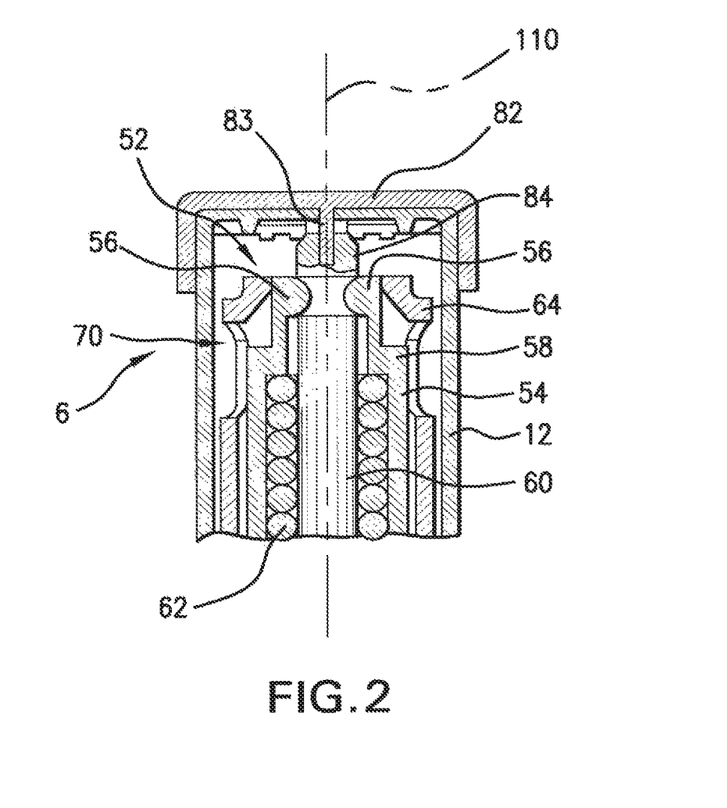
FIG. 2 is a cross-sectional view thereof, taken from a viewing perspective that is rotated 90° about the longitudinal axis of the injector from the perspective of FIG. 1.
Figure 3:
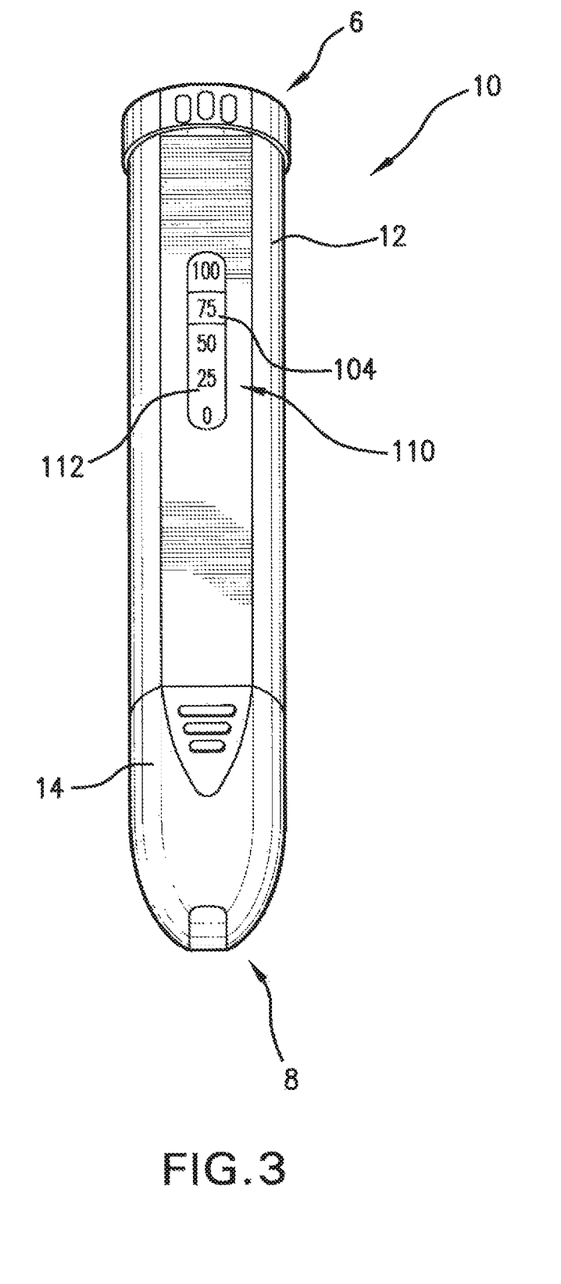
FIG. 3 is a perspective view of another embodiment of an injector.

Referring to FIGS. 1 and 2, trigger mechanism 52 is preferably also housed within outer housing 12. The trigger mechanism 52 includes an inner member, such as an inner housing 54, that can be attached to the outer housing 12, such as by snaps, an adhesive, a weld, or other known attachment. Trigger protrusions 56 extend inwardly from the proximal end of the inner housing 54 and are normally resiliently biased outwardly. Trigger protrusions 56 are received in a recess 58 of firing ram 60 in blocking association therewith. The trigger protrusions 56 prevent distal movement of the ram 60 prior to the firing of the injector 10 upon actuation of the trigger mechanism 52. The ram 60 is urged towards the distal end of the injector 10 by an energy source, which preferably is a compression spring 62, although other suitable energy sources can alternative be used such as elastomer or compressed-gas springs, or gas generators. A preferred type of compression spring is a coil spring.

A trigger member of the trigger mechanism 52, such as a latch housing 64, is provided exterior to the inner housing 54 to retain the trigger protrusions 56 in the blocking association in the recess 58 to prevent premature firing of the injector 10. The latch housing 64 is slideable inside the outer housing 12 with respect to the inner housing 54. preferably in an axial direction, and the latch housing 64 preferably surrounds the inner housing 54.

The distal end of the outer housing 12 preferably includes a needle guard 66 that is moveable with respect to the outer housing 12. The needle guard 66 is shown in FIG. 1 in a protecting position, in which the needle 24 is disposed within the guard 66. The needle guard 66 is retractable, preferably into the outer housing 12, in a proximal direction to an injecting position, in which the needle tip 26 and an end portion of the needle 24 is exposed for insertion into a patient. In the preferred embodiment, the proximal movement of the guard is substantially prevented at the injecting position. In embodiments where the container does not include a needle, the injection port and the distal end of the fluid chamber can he exposed upon retraction of the needle guard to the injecting position.

The needle guard 66 is associated with the latch housing 64 such that when the guard 66 is displaced distally it slides the latch housing 64 also in a distal direction to release the trigger protrusions 56 from the recess 58. Preferably, the latch housing 64 has a latching portion that abuts the inner housing 54 in an association to bias and maintain the trigger protrusions 56 positioned in the blocking association with the ram 60 prior to the firing of the injector 10, When the latch housing 64 is slid proximately by the retracting of the guard 66 to the injecting position, the latching portion slides beyond the portion of inner housing 54 that it contacts, allowing the trigger protrusions 56 to move radially outwardly from the recess 58 and therefore from the blocking association. When this happens, i.e., when the trigger mechanism 52 is actuated, the spring 62 biases the ram 60 against plunger 28 to fire the injector 10. Latch housing 64 preferably defines trigger openings 70 adjacent to the latching portions, which are configured to receive a portion of the inner housing 54, such as the surface disposed radially outwardly from the trigger protrusions 56.

The guard 66 is preferably resiliently biased distally towards the protecting position by compression coil spring 72. or other biasing member. Also, the needle guard 66 has an axial opening 74 to allow the needle 24 pass therethrough, and which may be sized according to the type of injector desired. In embodiments of the injector that do not include a needle, the axial opening can be sized to allow the distal end of the fluid chamber and injection port to pass therethrough. The construction of the embodiment of FIG. 1 allows a user to push the distal end of the injector 10 against the patient's skin, pushing the needle 24 into the skin at an injection location, substantially at the same speed as the injector is pushed. Once the needle 24 is fully inserted to an insertion point at a penetration depth, the trigger mechanism 52 fires the injection of medicament into an injection location.

Other embodiments can incorporate alternative trigger mechanisms for actuating firing of the injector. For example, the injector can include a button or other suitable depressible member on the outer housing that, upon depression thereof actuates firing of the injector.

Preferably, the injecting position of the guard 66 is such that a predetermined length of the end of needle 24 is exposed from the guard 66, In some embodiments, such as where the opening 74 is of a sufficiently large diameter, the skin of the patient maybe allowed to extend into the opening 74 when the device 10 is pressed there against, and a needle or injection port that does not protrude beyond the distal end of the guard 66 can he used. Some embodiments have a guard with a distal, skin-contacting surface that is discontinuous. In most embodiments where the injector includes a needle, the distance by which the needle tip extends past the distal end of the guard will be fairly close to the depth of the insertion of the needle.

In the preferred embodiment, such as for subcutaneous injection, the guard 66 is configured to allow insertion of the needle to a penetration depth in the skin that is up to about 5 mm below the skin surface, More preferably, the penetration depth is less than about 4 mm, and in one embodiment is less than about 3 mm. Preferably, the insertion depth is at least about 0.5 mm and more preferably at least about 1 mm. In another embodiment, the distance by which the needle. extends past the guard 66 or the distal surface. of the guard 66 that contacts the skin is up to about 5 mm, more preferably up to about 4 mm, and in one embodiment up to about 3 mm. Preferably, extension distance is at least about 0.5 mm, more preferably at least about 1 mm, and most preferably at least about 2 mm. In a preferred embodiment, tip 26 extends by a distance of around 2.5 mm beyond the portion of the guard 66 that contacts the skin in the injecting position.

In another embodiment, such as for intramuscular injection, the injector is configured to allow the needle to be inserted into the patient to a penetration depth in the skin, or alternatively beyond the distal surface of the guard, by a distance of up to about 15 mm. In one embodiment, this distance is about between 10 mm and 14 mm. In an embodiment for jet injection of epinephrine for instance, a preferred penetration depth or distance beyond the guard is between about 12 mm and 13.5 mm, and most preferably around 12.7 mm. Jet injection with this length needle improves the distribution of the medicament in the patient tissue compared to non-jet injection. Other exposed needle lengths can be selected for jet injection to different depths below the skin, with a preferred overall penetration length of between about 0.5 nun and about 20 mm. In these embodiments, the needle guard is preferably configured for retracting from a protecting position, preferably covering the entire needle, to an injecting position, in which the desired length of the end of the needle is exposed. In alternative embodiments, the needle tip stops behind or proximal to the guard, and penetrates the skin that is pushed into the guard.

In some embodiments, the energy source, which is preferably spring 62, and the container, which is preferably prefilled syringe 18, are configured to jet inject the medicament into the patient to an injection site. The spring 62 applies a force on the plunger 28 that is preferably sufficient to elevate the pressure within the fluid chamber 22 to a level high enough to eject the medicament from the needle 24 as a jet. Jet injection is to be understood as an injection with sufficient velocity and force to drive the medicament to locations remote from the needle tip 26 or injection port 25. The jet injector embodiments deliver a jet injection, the medicament is jet injected distally or in other directions, such as generally radially by the elevated pressure jet, which beneficially improves the distribution of the medicament after the injection and keeps a large bolus from forming that can detrimentally force the medicament to leak back out of the patient around the needle or through the hole left behind by the needle after it is removed. In alternative autoinjector embodiments that use needles, the injection pressures are relatively very low, and the medicament exits the needle tip inside the patient and is typically deposited locally around the needle in a bolus.

Preferably, in embodiments where needles are used, the needles are between 26 and 28 gage, and are most preferably around 27 gage, but alternatively other needle gages can be used where the other components are cooperatively configured to produce the desired injection. Preferably, the components of the injector 10 are configured to jet inject the medicament to a subterraneous injection site.

Preferred injection rates are below about 0.75 mL/sec., more preferably below about 0.6 mL/sec., and preferably at least about 0.2 mL/sec., more preferably at least about 0.3 mL/sec, and most preferably at least about 0.4 mL/sec. Preferably, the injection of the entire amount of medicament is completed in less than about 4 seconds, more preferably in less than about 3 seconds, and most preferably in less than about 2.5 seconds. Preferably, the medicament injection takes at least about 1 second, and more preferably at least 1.5 seconds, and most preferably at least about 1.75 seconds. A preferred embodiment injects the medicament at about 0.5 mL/sec., completing the injection of 1 mL, in about 2 seconds. Other alternative injection rates, injection volumes, and injections times can also be used.

The entire amount of medicament contained and injected from fluid chamber of the container is preferably between about 0.02 mL and 4 mL, and preferably less than about 3 mL, and in the preferred embodiment is around 1 mL. Larger volumes may also be selected depending on the particular medicament and dosage required. Preferably, the container 18 shown in FIG. 1 is assembled into the remaining parts of the injector 10 already containing the desired amount of medicament, In a preferred embodiment, the container 18 contains about 1 mL of medicament.

As shown in the preferred embodiment of FIG. 1, the injector 10 includes a volume-control mechanism 90 configured to select the fraction of medicament in the fluid chamber 22 that is to be injected, or correspondingly the dosage volume to be injected. The volume-control mechanism of this embodiment includes the rani 60, a cap 82, and a stopping member 100.

The ram 60, as previously described, preferably has a threaded portion 61 and is configured for rotating about its longitudinal axis 110 to permit the option of injecting less than all of the medicament. Stopping member 100 preferably includes a body portion 102, which can he configured as an internally threaded nut, and at least one lateral wing, and preferably two lateral wings 104 extending laterally, and preferably on opposing sides of the body portion 102. The body portion 102 is preferably in threaded association with the ram 60 and is longitudinally moveable there along. Each of the lateral wings 104 is preferably disposed and slideable within respective tracks 106 that extend longitudinally. Tracks 106 are preferably associated with or are defined in the outer housing 12, and are positioned in the embodiment shown on opposite lateral sides of the outer housing 12. Each of the tracks 106 preferably has a proximal end 107 and a distal end 108, which define a track length therebetween. Upon rotation of the ram 60. tracks 106 prevent rotation of the lateral wings 104 about the longitudinal axis 110. Consequently, the position of the body portion 102 moves or is adjusted proximally or distally longitudinally along the threaded portion 61 of the ram 60, the lateral wings 104 sliding in the tracks 106 therewith, In the preferred embodiment, the distal end 108 of the track 106 acts as a blocking member and prevents distal movement of the stopping member 100, and enlarged portion 101 of the ram 60 prevents proximal movement thereof, but other structures can alternatively be used for this purpose.

By rotating the ram 60, the stopping member 100 is positioned to limit the throw of the ram 60 when the injector 10 is fired, allowing the selection of volume of medicament to be injected from the fluid chamber 22. Upon actuation of the spring 62 by the trigger mechanism 52., the ram 60 is biased distally against the plunger 28, thus displacing plunger 28 in a distal direction to force medicament out of the fluid chamber 22. Movement of the rain 60 distally against the plunger 28, and thus the volume of medicament that is injected from the fluid chamber 22 (i.e., the injection volume), is limited by the lateral wings 104 of the stopping member 100. For example, the ram 60 can only move distally upon actuation of the spring 62 until the lateral wings 104 are stopped by the distal ends 108 of the tracks 106. At that point, further movement of the ram 60 in the distal direction is prevented. The position of the stopping member 100 along the ram 60 thus effectively controls the injection volume of medicament injected from the fluid chamber 22.

The operable member for rotating the ram 60 about the longitudinal axis 110 to adjust the longitudinal position of the stopping member 100 is preferably cap 82 that is preferably removeably engageable with the ram 60. The cap 82 preferably includes an engagement portion 83 configured for mating receipt within a receiving portion 84 of the ram 60. In this configuration, twisting or rotation of the cap 82 while the engagement portion 83 is received in the receiving portion 84 results in rotation of the ram 60 about the longitudinal axis 110. By manipulating the cap 82, the position of the stopping member 100 can be adjusted proximately or distally along the ram 60 to select the fraction of medicament that is desired to be injected from the fluid chamber 22. The engagement and receiving portions 83,84 are preferably non-circular to prevent or restrict axial rotation therebetween.

In the preferred embodiment, for example, the length of the tracks 106 is substantially equal to the length between the distal end 109 of the fluid chamber 22 and the distal end of the plunger 28. Thus, when cap 82 is twisted to position the stopping member 100 in its most proximal position along the ram 60 with the lateral wings 104 disposed against the proximal ends 107 of the tracks 106), actuation of the spring 62 causes the ram 60 to move distally against the plunger 28 as the lateral wings 104 slide along the entire length of the track 106 before abutting the distal ends 108 of the tracks, and the plunger 28 correspondingly is moved distally through the fluid chamber 22 to the distal end 109 thereof, injecting the entire volume of medicament therefrom.

If the cap 82 is twisted to position the stopping member 100 more distally along the cava 60, then the injection volume will only be a fraction of the entire volume of medicament in the fluid chamber 22 because upon actuation, the lateral wings 104 will slide along the tracks 106 and abut the distal ends 108 thereof to prevent the ram 60 from biasing the plunger 28 completely to the distal end 109 of the fluid chamber 22. As such, the entire volume of the medicament in the fluid chamber 22 is not injected. One of ordinary skill in the art would understand that the cap 82 can be twisted to adjust the position of the stopping member 100 relative to the ram 60 to select the appropriate injection volume of medicament that is desired to he injected.

Alternative embodiments can he provided with different throw and adjustment ranges to limit the range of adjustability to less than from 100% to 0% of the total volume of contained medicament. In one embodiment, the upper limit of volume fraction is less than 100%, about 90% or about 80%, and the lower limit is more than 0%, e.g., about 10%, 30%, or 50%. Additionally, other embodiments of the injector can include alternative mechanisms that are configured to limit the throw/adjustment ranges or the volume of medicament ejected from the injector.

Preferably, the outer housing 12 includes a window portion 111 adjacent the tracks 106 and along the length thereof, as shown in the preferred embodiment of FIG. 4. The window portion 111 is preferably made of a hard and durable, yet substantially transparent, material to allow the position of the lateral wings 104 of stopping member 100 to be visible therethrough. More preferably, the window portion 111 includes indicia 112 along and adjacent the length of the tracks that corresponds to the injection volume to be injected from the fluid chamber 22. For example, the indicia can include marking intervals between 0% to 100% (the 0% marking disposed adjacent the distal end 108 of the track and the 100% marking disposed adjacent the proximal end 107 of the track) such that adjusting the position of the stopping member 100 so that the lateral wings 104 are substantially aligned with a 75% marking indicates that the injection volume will be 75% of the entire volume of medicament contained in the fluid chamber 22.

One of ordinary skill in the art would understand that other such indicia or marking schemes can be used as desired. For example, indicia can be included on the housing adjacent the window rather than directly on the window, or the indicia can correspond to absolute values of injection volumes rather than percentages of the entire volume of medicament in the fluid chamber.

The preferred embodiment of the injector 10 shown in FIG. 1 also includes a bearing disposed between the spring 62 and the rain 60. The bearing is preferably an annular bushing 68, such as a nylon washer. The bushing 68 is configured for preventing or substantially reducing friction between the spring 62 and the ram 60 as the ram is rotated about the longitudinal axis 110, while still transferring biasing energy from the spring 62 to the ram 60 upon actuation of the spring.

While the preferred embodiments disclosed herein have been described in terms of a single-use injector (i.e., where a single injection volume of medicament is injected from a container prior to replacing the used container with a new container), one of ordinary skill in the art would understand that in other embodiments of the present invention, multiple injection volumes can be injected from the same container. For example, a first injection volume of 80% of the entire volume of medicament in the fluid chamber may be injected, followed by a subsequent injection of a second injection volume of the same or different fraction of the remaining volume of medicament in the fluid chamber.

The preferred embodiment is a single-use injector, being configured to prevent a user from reloading and reusing the injector. As such, the embodiment of FIG. 1 does not have a way of resetting the injector to fire again, and preferably cannot be reloaded to with another medicament container without substantial disassembly or breaking of the injector. An alternative embodiment, however, is a reusable injector that can be reset, such as by reloading the firing mechanism and reloading the medicament.

The content of International Application No. PCT/US2006/0002429, now WO 2006/079064, is hereby expressly incorporated herein by reference thereto. The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present invention.

What is claimed is:

1. An injector for injecting medicament in a patient, comprising:
    a container comprising a fluid chamber containing a first volume of a medicament;
    an injection conduit associated with the fluid chamber for defining a fluid pathway therefrom to inject the first volume of the medicament from the fluid chamber to an injection location;
    a trigger mechanism associated with the fluid chamber for expelling the first volume of the medicament from the fluid chamber through the injection conduit, the trigger mechanism comprising a threaded ram configured for biasing the first volume of the medicament in the fluid chamber for expelling the medicament;
    a volume-control mechanism operable by a user to select a fraction of the first volume of the medicament that is injected when the trigger mechanism is actuated to inject the first volume of the medicament wherein the volume-control mechanism comprises a stopping member in threaded association with the threaded ram; and
    a blocking member positioned to block distal movement of the stopping member associated with the threaded ram when the trigger mechanism is operated to expel the first volume of the medicament,
    wherein the threaded ram is rotatable with respect to the stopping member for selectively positioning the stopping member longitudinally along the threaded ram to select the fraction of the first volume of the medicament, and
    wherein the stopping member comprises two lateral members that protrude laterally from the threaded ram to a position longitudinally aligned with the blocking member.

2. The injector of claim 1, wherein the injection conduit comprises an injection-assisting needle.

3. The injector of claim 1, wherein the volume-control mechanism defines a track that extends generally longitudinally, the at least one of the lateral members being slidably received therein, wherein the at least one of the lateral members is configured to prevent rotation of the stopping member about a longitudinal axis when the threaded ram is rotated thereabout for repositioning the stopping member longitudinally along the threaded ram.

4. The injector of claim 3, further comprising an injector housing that defines the track, wherein the track has a distal end that comprises the blocking member.

5. The injector of claim 4, wherein the injector housing includes:
    a window adjacent a length of the track such that a longitudinal position of the stopping member within the injector is visible through the window; and
    indicia adjacent the window for determining a selected injection volume of the first volume to be injected.

6. The injector of claim 1, wherein the trigger mechanism further comprises an energy source activatable for expelling the first volume of the medicament, and the threaded ram is operably associated with the energy source such that the threaded ram is biased by the energy source when the trigger mechanism is activated.

7. The injector of claim 1, wherein the volume-control mechanism further comprises an exterior user-control associated with the threaded ram for rotating the threaded ram about a longitudinal axis to select an injection volume by selectively repositioning the stopping member longitudinally on the threaded ram.

8. The injector of claim 7, wherein the exterior user-control is configured for disengagement from the threaded ram when the trigger mechanism is activated to expel the first volume of the medicament.

9. The injector of claim 8, wherein:
the injector comprises a housing that houses the trigger mechanism; and
the exterior user-control includes a cap mounted on the housing and having a coupling engagement portion that extends into the housing and is rotationally fixed with the threaded ram for rotating the threaded ram by rotating the cap, wherein the coupling engagement portion is configured to disengage from the threaded ram when the threaded ram is driven away from the coupling engagement portion upon activation of the trigger mechanism.

10. The injector of claim 1, further comprising a bearing member disposed between an energy source and the threaded ram and configured for reducing friction therebetween when the threaded ram is rotated.

11. The injector of claim 1, wherein the injector is configured for single-use injection of first volume of the medicament therefrom.

12. The injector of claim 1, wherein the container is a prefilled syringe, and the injector further comprises an injection-assisting needle disposed in fluid communication with the fluid chamber, the injection-assisting needle having an injecting tip configured for piercing a patient's skin at the injection location.

13. The injector of claim 1, further comprising a retractable guard disposed at a distal end of the injector and movable from an extended position to an injecting position for activating the trigger mechanism.

14. The injector of claim 1, wherein the trigger mechanism further comprises an energy source activatable for expelling the first volume of the medicament, and the injection conduit is configured for jet injecting the first volume of the medicament.

15. The injector of claim 14, wherein the injection conduit comprises an injection-assisting needle.

16. The injector of claim 1, wherein the first volume of the medicament is epinephrine, atropine, sumatriptan, antibiotics, antidepressants, and anticoagulants.

17. An injector for injecting medicament in a patient, comprising:
a container comprising a fluid chamber containing a first volume of a medicament;
an injection conduit associated with the fluid chamber for defining a fluid pathway therefrom to inject the first volume of the medicament from the fluid chamber to an injection location;
a trigger mechanism associated with the fluid chamber for expelling the first volume of the medicament from the fluid chamber through the injection conduit, the trigger mechanism comprising a threaded ram configured for biasing the first volume of the medicament in the fluid chamber for expelling the medicament;
a volume-control mechanism operable by a user to select a fraction of the first volume of the medicament that is injected when the trigger mechanism is actuated to inject the first volume of the medicament wherein the volume-control mechanism comprises a stopping member in threaded association with the threaded ram; and
a blocking member positioned to block distal movement of the stopping member associated with the threaded ram when the trigger mechanism is operated to expel the first volume of the medicament,
wherein the threaded ram is rotatable with respect to the stopping member for selectively positioning the stopping member longitudinally along the threaded ram to select the fraction of the first volume of the medicament, and
wherein the stopping member comprises two lateral members that protrude laterally from the threaded ram to a position longitudinally aligned with the blocking member,
wherein the volume-control mechanism defines a track that extends generally longitudinally, the at least one of the lateral members being slidably received therein, wherein the at least one of the lateral members is configured to prevent rotation of the stopping member about a longitudinal axis when the threaded ram is rotated thereabout for repositioning the stopping member longitudinally along the threaded ram.

* * * * *